(12) United States Patent
Ryan (10) Patent No.: US 7,926,368 B2
(45) Date of Patent: Apr. 19, 2011

(54) HUMIDITY-CONTROLLED GAS-BORNE MATTER COLLECTION DEVICE

(75) Inventor: Scott Ryan, Ocala, FL (US)

(73) Assignee: Zefon International, Inc., Ocala, FL (US)

( * ) Notice: Subject to any disclaimer, the term of this patent is extended or adjusted under 35 U.S.C. 154(b) by 622 days.

(21) Appl. No.: 11/977,820

(22) Filed: Oct. 26, 2007

(65) Prior Publication Data

US 2008/0233636 A1 Sep. 25, 2008

Related U.S. Application Data

(60) Provisional application No. 60/855,868, filed on Nov. 1, 2006.

(51) Int. Cl.
*G01N 1/04* (2006.01)

(52) U.S. Cl. ........................... 73/864.71; 73/28.05

(58) Field of Classification Search ............... 73/29.01, 73/31.02, 863.42, 863.71, 864.51, 864.52, 73/864.71, 864.91, 28.05; 435/30

See application file for complete search history.

(56) References Cited

U.S. PATENT DOCUMENTS

| | | | | | |
|---|---|---|---|---|---|
| 2,522,952 | A | * | 9/1950 | Krohn | 312/31.1 |
| 2,546,599 | A | * | 3/1951 | Hicks | 312/31.1 |
| 2,680,048 | A | * | 6/1954 | McDonald | 312/31.1 |
| 3,001,914 | A |   | 3/1956 | Andersen | |
| 2,819,135 | A | * | 1/1958 | Shapiro | 312/31.1 |
| 3,081,137 | A | * | 3/1963 | Kolokythas | 96/148 |
| 3,127,329 | A | * | 3/1964 | Andersen | 435/5 |
| 3,336,093 | A | * | 8/1967 | Phelps | 312/31.1 |
| 3,892,130 | A | * | 7/1975 | Winget et al. | 73/864.62 |
| 3,903,745 | A | * | 9/1975 | Bolser | 73/863.21 |
| 3,932,220 | A |   | 1/1976 | Liotta | |
| 3,940,250 | A |   | 2/1976 | Plakas et al. | |
| 3,956,070 | A | * | 5/1976 | Kenyon | 435/30 |
| 3,958,938 | A | * | 5/1976 | Doonan et al. | 435/30 |
| 3,968,012 | A | * | 7/1976 | Jones | 435/309.1 |
| 4,008,930 | A | * | 2/1977 | Swainson | 312/31.1 |
| 4,038,057 | A |   | 7/1977 | Roth | |
| 4,283,498 | A | * | 8/1981 | Schlesinger | 600/573 |
| 4,663,293 | A | * | 5/1987 | Hempel et al. | 435/309.1 |
| 4,761,379 | A | * | 8/1988 | Williams et al. | 600/573 |
| 4,783,401 | A |   | 11/1988 | Horan et al. | |
| 4,786,472 | A | * | 11/1988 | McConnell et al. | 422/61 |
| 4,883,644 | A |   | 11/1989 | Perlman | |
| 5,268,460 | A |   | 12/1993 | Thorne et al. | |
| 5,308,758 | A | * | 5/1994 | Dahl | 435/30 |
| 5,333,511 | A | * | 8/1994 | Boyum et al. | 73/864.34 |
| 5,360,722 | A | * | 11/1994 | Inoue et al. | 435/34 |
| 5,421,214 | A |   | 6/1995 | Burgdorfer | |
| 5,432,094 | A | * | 7/1995 | Delente | 436/127 |
| 5,529,914 | A |   | 6/1996 | Hubbell et al. | |
| 5,545,841 | A | * | 8/1996 | Wilfinger et al. | 174/17.08 |

(Continued)

OTHER PUBLICATIONS

Grinshpun, Ph.D, Sergey A., Gorny Ph.D., Rafal L.; Mainelis, Ph.D, Gediminas, "Evaluation Of The New EMS Impactor", University of Cincinnati Environmental Health Foundation, Apr. 12, 2001, 6 pages.

(Continued)

*Primary Examiner* — John Fitzgerald
(74) *Attorney, Agent, or Firm* — Foley & Lardner LLP (57) ABSTRACT

A system includes a device for collecting gas-borne matter therein and a humectant provided external to the device for maintaining a desired humidity level for collected matter in the device.

24 Claims, 8 Drawing Sheets

U.S. PATENT DOCUMENTS

| | | | |
|---|---|---|---|
| 5,556,579 A * | 9/1996 | Newman | 261/99 |
| 5,589,154 A | 12/1996 | Anderson | |
| 5,693,895 A | 12/1997 | Baxter | |
| 5,780,295 A | 7/1998 | Livesey et al. | |
| 5,831,182 A * | 11/1998 | Swenson | 73/863.22 |
| 5,840,573 A | 11/1998 | Fields | |
| 5,905,038 A * | 5/1999 | Parton | 435/287.6 |
| 5,975,288 A * | 11/1999 | Crowder et al. | 206/205 |
| 6,047,701 A * | 4/2000 | Feldman | 131/303 |
| 6,157,306 A * | 12/2000 | Mularoni | 340/602 |
| 6,218,191 B1 * | 4/2001 | Palander | 436/63 |
| 6,406,906 B1 | 6/2002 | Herbig et al. | |
| 6,514,721 B2 | 2/2003 | Spurrell | |
| 6,692,953 B1 * | 2/2004 | Sugita et al. | 435/309.1 |
| 6,925,853 B2 | 8/2005 | Radolovich | |
| 7,153,475 B2 * | 12/2006 | Hill et al. | 422/88 |
| 7,205,145 B2 * | 4/2007 | Ryan | 435/309.1 |
| 2002/0066321 A1 | 6/2002 | Lagraff et al. | |
| 2002/0160440 A1 * | 10/2002 | McDonnell et al. | 435/31 |
| 2003/0068777 A1 | 4/2003 | Nakano et al. | |
| 2003/0207304 A1 | 11/2003 | Black et al. | |
| 2004/0058428 A1 | 3/2004 | Perlman et al. | |
| 2004/0185554 A1 | 9/2004 | Daitch et al. | |
| 2006/0127966 A1 * | 6/2006 | Ryan | 435/30 |
| 2006/0128008 A1 * | 6/2006 | Ryan | 435/287.9 |

OTHER PUBLICATIONS

Macher, Sc.D., M.P.H., Janet M. and Burge, Ph.D, Harriet A., "Sampling Biological Aerosols", Environmental Health Laboratory, California Department of Health Services, Berkeley California; Department of Environmental Health, Harvard School of Public Health, Boston, Massachusetts, Chapter 22, pp. 661-701, Feb. 2006.

Sartorius, "Collecting Airborne Viruses and Phages Using The Gelatin Membrane Filter Method", Sartorius AG Invention Technology, 10 pages, Feb. 2006.

Zefon International Inc., Zefon Aerotech 6™ Operating Manual "Viable Microbial Particle Sampler", available at www.zefon.com, 4 pages, Feb. 2006.

* cited by examiner

HUMIDITY-CONTROLLED GAS-BORNE MATTER COLLECTION DEVICE

CROSS-REFERENCE TO RELATED PATENT APPLICATIONS

The present application claims the benefit under 35 U.S.C. §119(e) of U.S. Provisional Patent Application No. 60/855,868 filed Nov. 1, 2006.

The following applications are incorporated by reference herein in their entirety, including the drawings, claims, description, and abstract thereof: U.S. Provisional Patent Application No. 60/855,868; U.S. patent application Ser. No. 10/857,290; U.S. patent application Ser. No. 10/857,240; U.S. Provisional Patent Application No. 60/473,841; U.S. patent application Ser. No. 11/348,222; U.S. patent application Ser. No. 11/348,051; and U.S. patent application Ser. No. 10/808,114.

BACKGROUND

The present invention relates generally to the field of airborne matter collection devices.

Air sampling devices are generally used to determine the quantity and types of matter present in a gas (e.g., air or other gaseous atmospheres). For example, in a factory where materials are used that may be detrimental to human health, it may be desirable to determine the amount and types of matter present in the atmosphere so that factory workers are not exposed to unsafe or undesirable levels of airborne materials. In other examples, air sampling devices may be used in a variety of environments, including, but not limited to, office buildings, houses, hospitals, clean rooms, or outdoors.

Sampling devices conventionally include a collection device (e.g., a particle impaction device, microscope slide, petri dish, or other device) for collecting and retaining matter included in the gas being sampled. In use, the sampling device draws a gas (e.g., air) toward the collection device. Matter (e.g., viable and/or non-viable matter) included in the gas impacts a substance or material (e.g., a collection medium) provided on or in the collection device, where the matter is retained until analysis can be performed. One known type of collection device is a cassette or cartridge type sampling device, such as the Air-O-Cell product manufactured by Zefon International, Inc. of Ocala, Fla.

One difficulty associated with the use of some known collection devices is that the collection devices may become contaminated with continued use. For example, after sampling is complete, the collection medium (e.g., agar medium) is removed from the collection device and the collection device is cleaned. Remnants of past samples and media may remain after cleaning, which may affect results of subsequent sampling.

Another difficulty with conventional collection devices is that moisture levels may be uncontrolled near the collection medium. It is desirable, especially in the case of living organisms, that the sampled matter be maintained at an appropriate moisture level such that the sample neither dehydrates nor is over-hydrated to the point that the organisms continue to grow. In either case, such situations may lead to inaccurate information concerning the sampled matter.

One potential solution is the use of a dessicant to remove moisture in the vicinity of the collection medium. However, dessicants tend to simply dehydrate the collected matter instead of maintaining humidity at a desired level, which may not be suitable for living organisms.

It would be desirable to provide a relatively simple and inexpensive system for controlling the moisture level of sampled gas-borne matter to prevent dehydration and growth (i.e., to maintain the moisture level at an equilibrium level that is suitable for maintaining the samples without promoting growth). It would also be desirable to provide a system for storing and/or shipping sampled matter that maintains the moisture level of the sampled material.

SUMMARY

An exemplary embodiment relates to a system that includes a device for collecting gas-borne matter therein and a humectant provided external to the device for maintaining a desired humidity level for collected matter in the device.

Another exemplary embodiment relates to a system for controlling the humidity in a gas-borne matter collection device. The system includes a member configured for coupling to a gas-borne matter collection device and a material provided within the member for maintaining a predetermined level of humidity within the collection device.

Another exemplary embodiment relates a system that includes a housing configured for selective coupling to a gas-borne matter collection device. A humectant material is provided within the housing for maintaining a predetermined level of humidity within the collection device. The housing includes a structure for physically containing the humectant material while allowing two-way vapor transmission between the humectant material and the collection device.

Another exemplary embodiment relates to a system for collecting viable gas-borne matter that includes a sampling cassette including at least one inlet, at least one outlet, and a plate provided intermediate the inlet and outlet. A substance is provided on the plate for capturing viable matter carried in a gas drawn through the at least one inlet. A cap is configured for coupling to the cassette, and a humectant is provided in the cap for maintaining a predetermined level of humidity within the cassette. The system also includes a membrane provided between the humectant and the cassette that allows gas and vapor to move between the substance and the humectant. The humectant is configured to regulate the water activity level such that viable matter is maintained in a living state without promoting growth of such viable matter.

Another exemplary embodiment relates to a system that includes a container, a gas-borne matter collection device provided within the container, and a humectant material provided within the container. The humectant material is configured to maintain a humidity level within the container and within the gas-borne matter collection device.

BRIEF DESCRIPTION OF THE DRAWINGS

FIG. 1 is a perspective view of a collection device in the form of a sampling cassette according to an exemplary embodiment.

FIG. 2 is an exploded perspective view of the collection device shown in FIG. 1.

FIG. 3 is another exploded perspective view of the collection device shown in FIG. 1.

FIG. 4 is a cross-sectional view of the collection device shown in FIG. 1, the cross-sectional view being taken across line 4-4 in FIG. 1.

FIG. 5 is a perspective view of a cap coupled to the collection device shown in FIGS. 1-4 according to an exemplary embodiment.

FIG. 6 is a perspective view of the cap shown in FIG. 5.

DETAILED DESCRIPTION

With reference to FIGS. 1-4, a collection device or apparatus 10 is shown according to an exemplary embodiment that is configured for use with a pump or other air sampling device (not shown). Collection device 10 is shown in the form of a cassette or cartridge, although various configurations for may be used according to other exemplary embodiments.

According to an exemplary embodiment, collection device 10 is configured for use with a sampling device that draws air or other gases through the collection device (e.g., using an impeller, blower fan, or other type of fan or pump) to collect matter contained in or carried by the air or gases. According to other exemplary embodiments, other configurations for the collection device may be used, which may or may not require the use of a sampling device. One exemplary embodiment of such a sampling device is described in U.S. patent application Ser. No. 10/857,240, filed May 28, 2004, the entire disclosure of which is incorporated herein by reference.

Collection device 10 includes a top or upper portion 20, a bottom or lower portion 40, and a sampling plate or slide 50. Collection device 10 may be disassembled by decoupling top portion 20 and bottom portion 40 to allow removal of plate 50 after sampling has been completed. Top portion 20 and bottom portion 40 may be made from a variety of materials, including polymeric, metal, ceramic, glass, or other materials suitable for use in a collection device.

According to an exemplary embodiment, collection device 10 has a size and shape configured for coupling with a sampling device. For example, a rubber grommet tubing or other feature of the sampling device may couple to collection device 10 to relatively securely retain collection device 10 in place.

According to the exemplary embodiment shown in FIGS. 1-4, collection device 10 has a relatively cylindrical shape. According to other exemplary embodiments, other sizes and shapes for the collection device may be used. For example, according to another exemplary embodiment, a collection device may have a rectangular solid or cubic shape.

Figure 1:
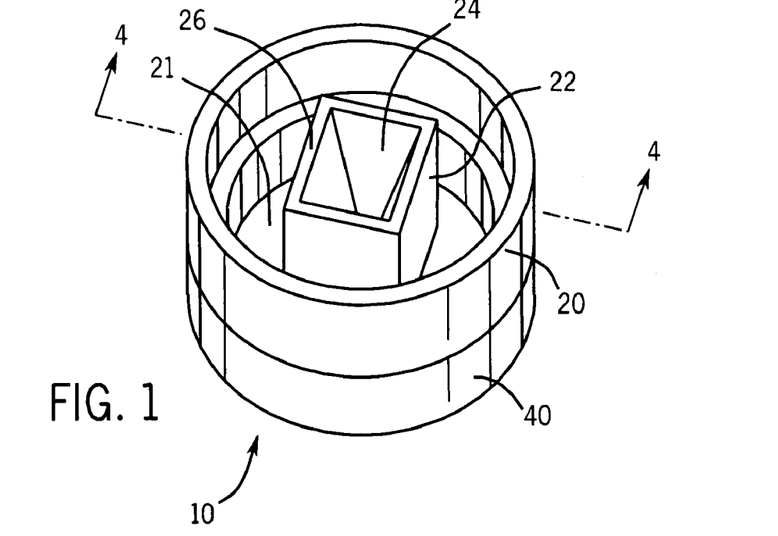
Figures 2, 3:
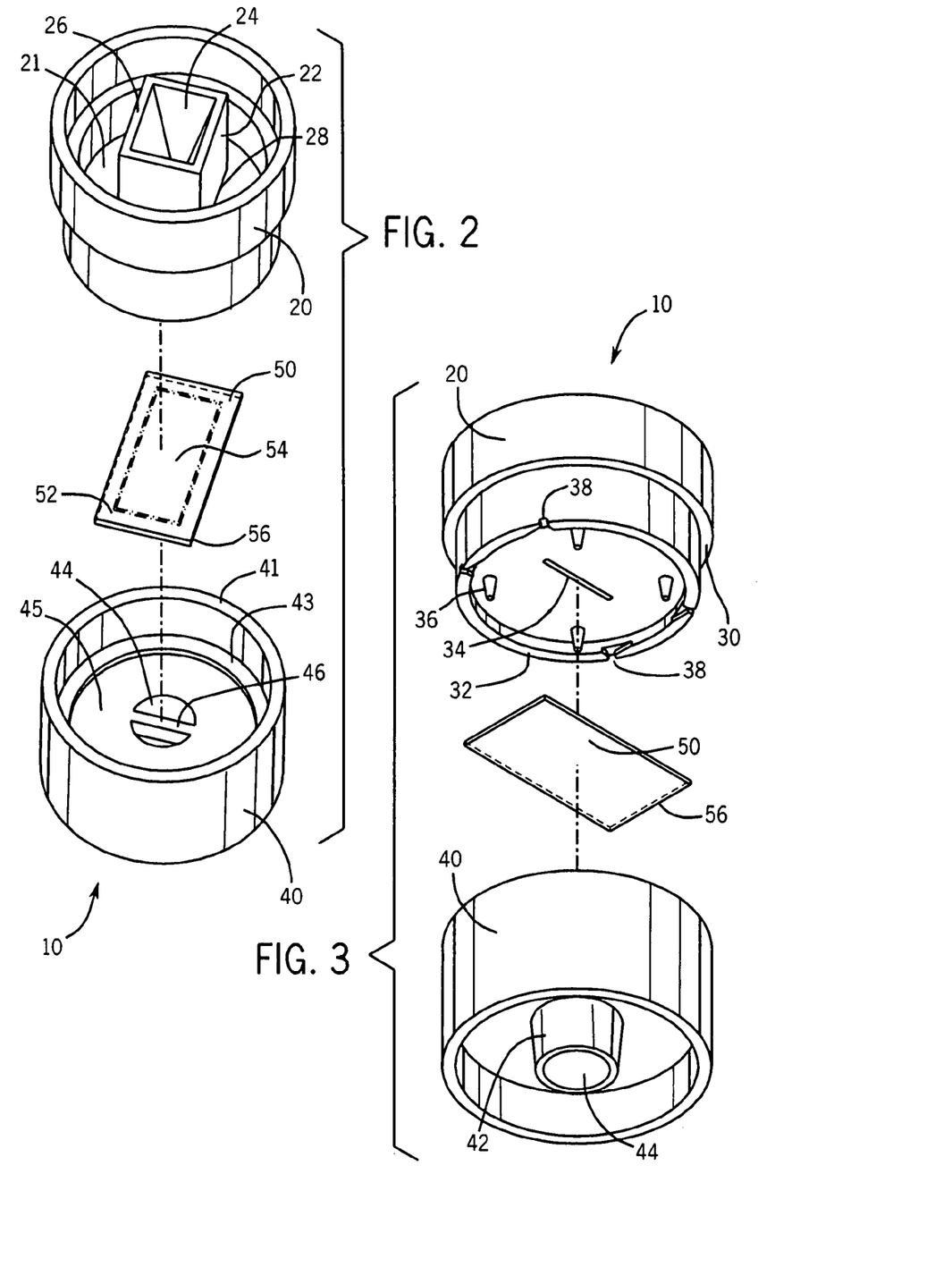
Figure 4:
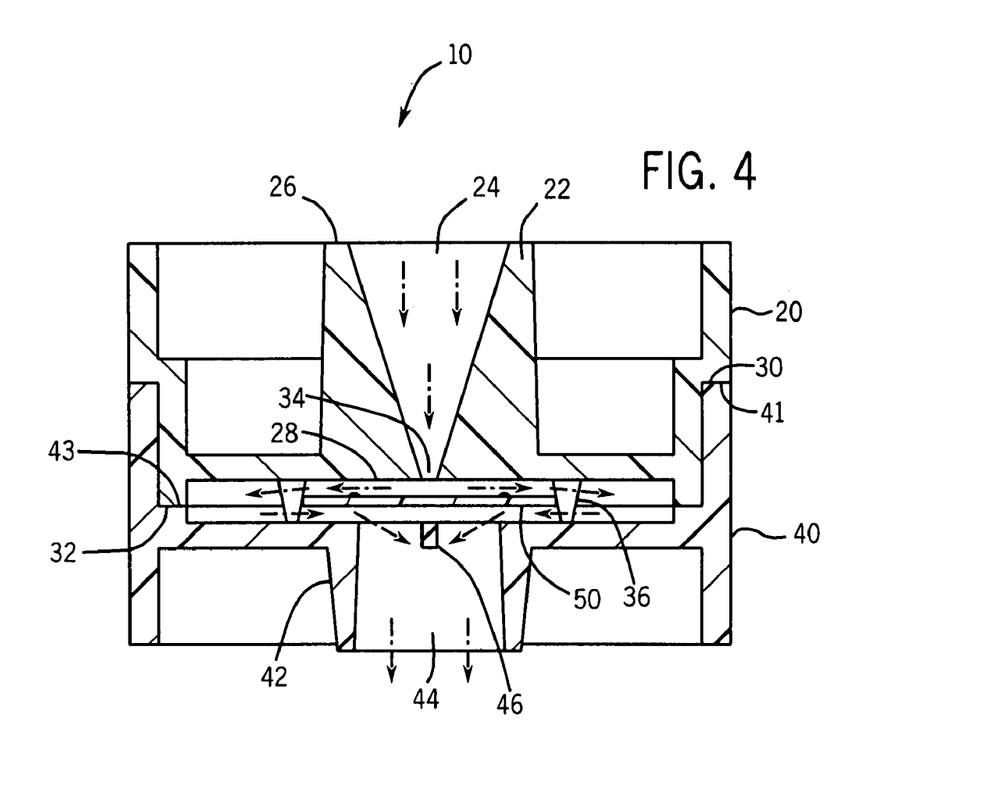
Figures 5, 7:
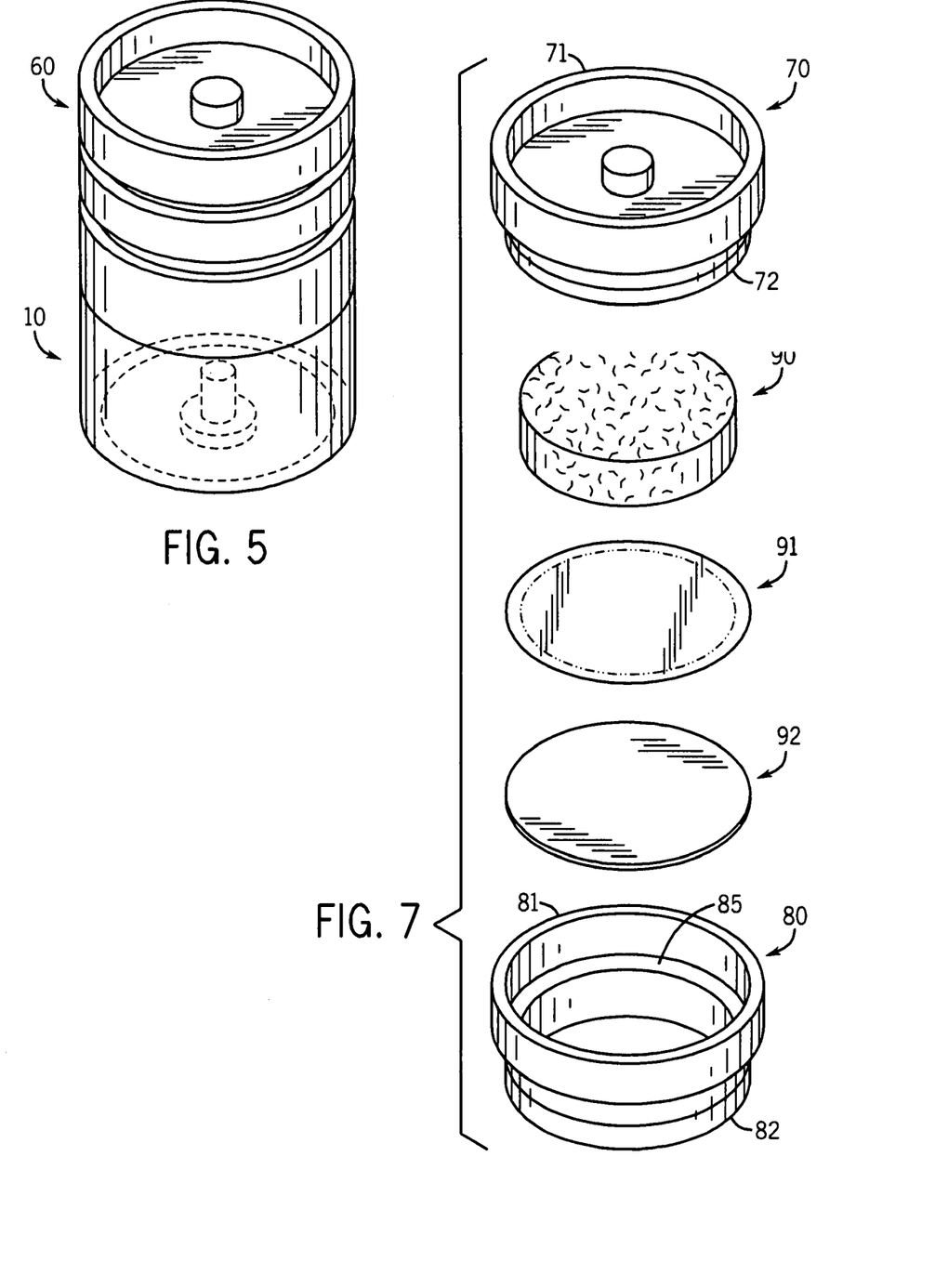
FIG. 7 is an exploded perspective view of the cap shown in FIG. 5.
Figures 6, 8:
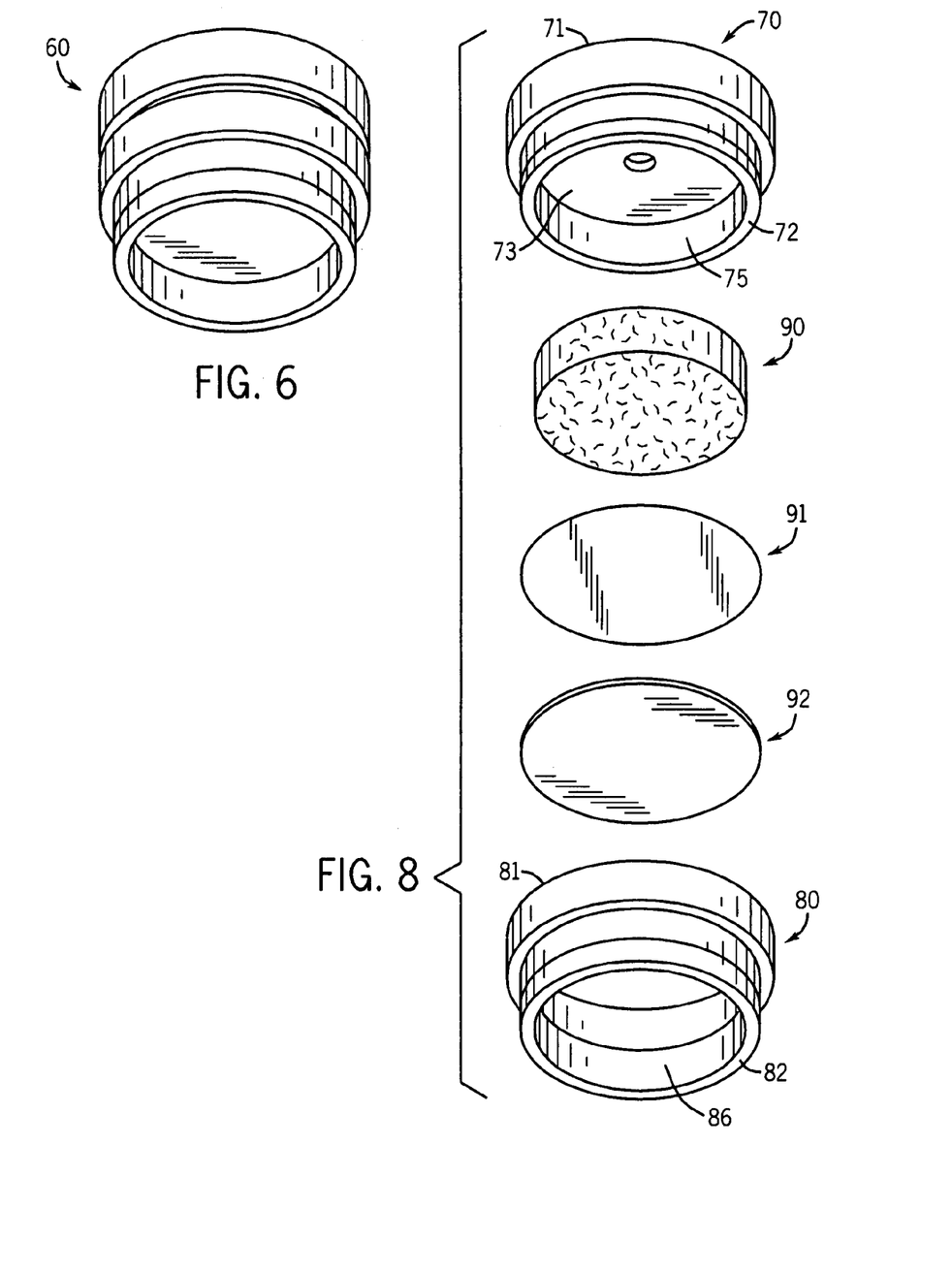
FIG. 8 is another exploded perspective view of the cap shown in FIG. 5.

Top portion 20 includes an inlet 22 that defines an aperture or opening 24 through which gas is drawn during sampling. According to an exemplary embodiment, the size of aperture 24 defined by inlet 22 narrows from a top portion 26 to a bottom portion 28 of inlet 22. Aperture 24 has a generally rectangular shape when viewed in the axial direction. The size (e.g., area) of the rectangle decreases from top portion 26 to bottom portion 28 in a substantially continuous manner. According to an exemplary embodiment, the width of aperture 24 (e.g., the longer side of the rectangle) remains constant between top portion 26 and bottom portion 28 while the length (e.g., the shorter side of the rectangle) decreases with increasing distance from top portion 26. As shown in FIG. 4, a cross-sectional view of inlet 22 taken along line 4-4 in FIG. 1 shows that aperture 24 has a generally trapezoidal shape when viewed in the longitudinal direction due to the decreasing size of aperture 24 with increasing distance from top portion 26. Aperture 24 thus narrows to form a slit 34 in a surface 21 of top portion 20.

According to another exemplary embodiment, both the length and width of the rectangle forming the aperture decrease with increasing distance from the top of the inlet. According to other alternative embodiments, the shape of the inlet and/or aperture may differ. For example, an aperture may have a generally circular, square, oval, or other shape when viewed in the axial direction. Such inlets and/or apertures according to alternative embodiments may or may not decrease in area with increasing distance from the top of the inlets. For example, where an aperture and/or inlet is provided with a generally circular cross-section viewed in the axial direction, the aperture and/or inlet may resemble a funnel (e.g., the area decreases with increasing distance from the top of the inlet) or may resemble a cylinder (e.g., the area does not decrease with increasing distance from the top of the inlet). Any of a variety of shapes and configurations may be provided for the aperture and/or inlet according to various other embodiments, and the shape, size, and other characteristics may be optimized for a particular application.

Bottom portion 40 of collection device 10 includes an outlet or exit port 42 defining an aperture or opening 44 through which air is drawn during sampling. A beam or bar 46 is provided across aperture 44 and is integrally formed with a surface 45 provided in bottom portion 40. Beam 46 acts as a stop to prevent objects from being inserted through aperture 44, which might otherwise collide with and damage or destroy plate 50.

According to an exemplary embodiment, outlet 42 has a generally circular shape when viewed in the axial direction and tapers from a larger diameter to a smaller diameter with increasing distance from a surface 45 provided in bottom portion 40. According to alternative embodiments, the size and/or shape of outlet 42 may differ. For example, according to another exemplary embodiment, the outlet may have a generally square or oval shape when viewed in the axial direction. Further, the outlet may or may not taper along its length.

While collection device 10 is shown as having a single outlet and a single inlet, according to other exemplary embodiments, any number of outlets and inlets may be provided in a collection device having any of a variety of different configurations (e.g., one outlet may have a relatively circular opening while a second outlet may have a relatively rectangular opening, etc.). A sampling plate or slide may have different sampling mediums (e.g., suspension media) provided in different areas such that a different sampling medium is provided adjacent each of the plurality of inlets.

When collection device 10 is assembled, a portion of top portion 20 is inserted within bottom portion 40 such that a first rim or surface 30 provided on top portion 20 abuts a first rim or surface 41 provided on bottom portion 40 and a second rim or surface 32 provided on top portion 20 abuts a second rim or surface 43 provided on bottom portion 40. Plate 50 is provided intermediate a top portion 20 and a bottom portion 40 of collection device 10 (and hence between inlet 22 and outlet 42). A top surface 52 of plate 50 is provided adjacent or proximate slit 34 formed in bottom surface 21 of top portion 20. According to other exemplary embodiment, other ways of connecting the top portion to the bottom portion may be utilized (e.g., glue, fasteners such as screws and bolts, welding, etc.).

To secure plate 50 in relation to inlet 22 and slit 34, projections or protrusions 36 extend outward from bottom surface 21 of top portion 20. Plate 50 is positioned between projections 36 such that projections 36 prevent lateral movement of plate 50. Additionally, corners 56 of plate 50 are received within cutouts 38 included in second rim 32 of top portion 20 to further restrict movement of plate 50 and to secure plate 50 in a relatively fixed relationship to inlet 22 and slit 34. While plate 50 is shown as having a particular shape in the accompanying FIGURES, according to other exemplary embodiments, the plate or slide may have any of a variety of sizes, shapes, and/or configurations (e.g., oval, circle, hexagon, etc.), which may be chosen based on any of a variety of factors (e.g., required size of sampling area, manufacturability, cost, etc.).

Other means of securing the plate in place may be utilized according to other embodiments. For example, either projections or cutouts may be omitted from the collection device. In another example, where a plate having a different size or shape is utilized, a different number of cutouts and/or projections may be utilized. In yet another example, neither cutouts nor projections are provided, and the plate is secured in place by a different type of feature or structure. In yet another example, the plate may be glued (e.g., using an adhesive) or ultrasonically welded in place. Any feature or structure that retains the plate in place may be utilized according to various embodiments.

While the FIGURES illustrate a collection device 10 that includes a top portion 20 that is inserted into a bottom portion 40, according to another exemplary embodiment a bottom portion may be inserted into a top portion. According to another embodiment, neither of the top and bottom portions are inserted into each other, and coupling of the top portion and bottom portion is accomplished by any of a variety of other methods. According to various other embodiments, the top and bottom portions may be secured together using adhesives, ultrasonic welding or sealing, a screw-type arrangement, a snap-fit type arrangement, or any other suitable means.

Plate 50 may be made of any suitable material, including glass, porous glass fiber filters, ceramic, porous plastic, metal (e.g., aluminum, steel, etc.), or any other suitable material (e.g., a porous rigid material). According to an exemplary embodiment, plate 50 is made of glass and has a generally rectangular shape. Plate 50 is relatively thin (e.g., between approximately 0.001 and 0.125 inches), although the thickness may vary in alternative embodiments. For example, the plate may be formed to have a thickness similar to that of conventional microscope slides. Other configurations may also be used for plate 50. For example, the plate may be made of a polymeric material and/or may be formed in the shape of an octagon, triangle, square, circle, oval, or any other suitable shape (e.g., cup-shaped, dish-shaped, etc.).

According to an exemplary embodiment, collection device 10 is a disposable or non-reusable type collection device (i.e., collection device 10 is intended as a single-use type component that is discarded after use). According to other exemplary embodiments, collection device 10 may be a reusable type collection device (e.g., the plate may be cleaned and re-inserted into the collection device or the plate may be replaced with a new plate). After sampling is complete, collection device 10 is disassembled to remove plate 50 from collection device 10 so that the matter retained in substance 54 may be quantified, tested, or otherwise analyzed. One advantageous feature of using a disposable collection device is that cleaning of the plate (e.g., removal of the suspension medium (e.g., substance 54) and captured viable matter and deposition of new or fresh suspension medium) is eliminated. A related advantageous feature of using a disposable collection device is that errors in sampling due to contamination of the suspension medium and/or to variations in application of new suspension medium material to the plate may be reduced or eliminated. According to another exemplary embodiment, plates (e.g., glass slides, etc.) may be provided as separate components for use in a collection device and sold separately from the collection device.

FIG. 4 shows a cross-sectional view of collection device 10 taken in the longitudinal direction along line 4-4 in FIG. 1. Gas flow through collection device 10 is indicated generally by dashed arrows. As shown, gas is drawn into collection device 10 through inlet 22. The velocity of the air increases as it approaches bottom portion 28 of inlet 22 due to narrowing of aperture 24. The gas then travels around plate 50 and through outlet 42. At least a portion of the gas-borne matter drawn into inlet 22 is captured by a substance or material 54 (e.g., a suspension or transport medium) provided on plate 50 when the gas changes direction to travel around plate 50.

Substance 54 is provided on top surface 52 of plate 50 and is aligned with slit 34 such that matter carried in a gas impacts substance 54 when gas is drawn through inlet 22 during sampling. In this manner, gas-borne viable and/or non-viable matter may be captured by substance 54.

Substance 54 may be any suitable collection medium according to various exemplary embodiments, non-limiting examples of which are described in U.S. patent application Ser. No. 10/808,114, filed Mar. 24, 2004, the entire disclosure of which is incorporated herein by reference. According to one exemplary embodiment, substance 54 is configured to maintain viable matter (e.g., biological organisms such as mold spores, bacteria, skin cells, anthrax, viruses, insects and insect parts, and other viable matter) in a living state without promoting growth of such viable matter. For example, substance 54 is configured to provide hydration for viable matter included therein to prevent the viable matter from drying out and/or dying when retained within substance 54.

According to an exemplary embodiment, substance 54 is configured to maintain viable matter in a living state for at least a predetermined amount of time (e.g., between approximately 1 and 14 days). For example, mold spores captured in the substance 54 may be kept alive in substance 54 for between approximately 2-7 days before growth may appear. The specific amount of time viable matter may be kept alive may depend on a number of factors, including the type of viable matter (e.g., mold spores, viruses, bacteria), the composition of the substance, the temperature of the sample, and other factors.

To prevent contamination of substance 54 with nutrients or other development-promoting materials during shipping and/or storage, collection device 10 may be sealed. For example, collection device 10 may be vacuum sealed and/or may include elements that cover inlet and 22 and outlet 42 to prevent introduction of any airborne nutrients. According to an exemplary embodiment, stickers or labels are provided to cover openings 24 and 44 during shipping and storage. According to another exemplary embodiment, caps or plugs may be provided to cover openings 24 and 44. Such stickers, labels, caps, or plugs are removed before sampling to allow the flow of gas through collection device 10, and may be replaced after sampling is completed to prevent contamination of the sample. Collection device 10 may also be shipped and/or stored in a sealed (e.g., vacuum sealed) pouch or container to further prevent contamination and reduce drying of the substance that acts as a suspension medium.

When sampling is completed, collection device 10 may be disassembled to remove plate 50 (and hence the suspension medium and captured viable matter). Plate 50 may be removed from collection device 10 immediately after sampling is complete, or may remain in the collection device during shipping of the collection device to a remote location (e.g., a lab) or during storage. It may be desirable to seal the collection device until it is desired to remove the plate from the collection device (e.g., by re-attaching a label, sticker, plug, or cap over apertures 24 and 44 to prevent contamination of substance 54 and viable matter captured therein).

To remove viable matter from substance 54, a liquid (e.g., water, peptone solution, etc.) is utilized. According to an exemplary embodiment, substance 54 is removed from plate 50 (e.g., by scraping) and placed in a liquid to separate the substance 54 from the viable matter. According to another exemplary embodiment, the entire plate 50, including substance 54, is placed in a liquid to remove substance 54 from plate 50 and the viable matter from substance 54. According to another exemplary embodiment, liquid may be introduced into the collection device 10 to remove substance 54 from plate 50 and the viable matter from substance 54. In any of these embodiments, the container or collection device holding the liquid may be vibrated or shaken (e.g., using a vortexer or other device, by hand, etc.) to hasten separation of viable matter from substance 54. According to still another exemplary embodiment, no vibration or shaking may be used, and the substance 54 will dissolve in water or another liquid, after which the water may be sampled.

With reference to FIGS. 5-8, a member or element 60 (shown in the form of cap or container) configured for use with a collection device 10 is shown according to an exemplary embodiment. Member 60 is configured to maintain a humidity or moisture level within the collection device 10. One advantageous feature of the exemplary embodiments shown in FIGS. 5-8 is that the water activity level (aW %) within the collection device 10 is regulated near a predetermined level, which may improve the accuracy of sampling by maintaining an appropriate sample size. For example, using a material such as a humectant, collected viable matter is maintained in a living state without promoting growth of such viable matter. The aW % is the amount of water in a substance available for use and as those reasonably skilled in the art would be aware, an appropriate low level will stop organisms from growing while enough moisture would still be present to maintain the organisms in a living state.

According to an exemplary embodiment, the member 60 may be provided to cover aperture(s) 24 and/or 44 and may be in a shape similar to collection device 10. Member 60 includes a top portion or part 70, a bottom portion or part 80, a material 90 (e.g., a humectant), a first membrane or filter 92, and a second membrane or filter 91. When member 60 is assembled, a portion of top part 70 is inserted within bottom part 80 such that a first rim or surface 71 provided on top part 70 abuts a first rim or surface 81 provided on bottom part 80 and a second rim or surface 72 provided on a top part 70 abuts a second rim or surface 82 provided on bottom part 80. Top part 70 and bottom part 80 may be made from a variety of materials, including polymeric, metal, ceramic, glass, or other materials suitable for use in a collection device.

The top part 70 may include a hollow area or space 75 formed or defined by the second rim 72 and a top surface 73. The material 90 may be inserted into the hollow area 75. The second membrane 91 may be provided adjacent or in contact with the humectant and the second rim 72. The first membrane 92 may be configured to be provided adjacent or in contact with the second membrane 91 and may be of the same approximate shape.

The bottom part 80 may include a first hollow area or space 85 formed by the first rim 81 and a second hollow area or space 86 formed by the second rim 82. The first rim 82 may be configured to be provided adjacent or in contact with the second membrane 91. When the member 60 is assembled the first hollow area 85 may be configured to allow the second rim 72, the material 90, the first membrane 92 and the second membrane 91 to be partially enclosed within the inner area of the member 60.

According to an exemplary embodiment as shown in FIGS. 5-8, the member 60 may be configured to cover aperture 24 of a collecting device 10. The bottom part 80 may be inserted within top portion 20 such that the first rim 81 abuts a first rim or surface 23 provided on top portion 20 and the second rim 82 abuts a second rim or surface 25 provided on top portion 20.

Any of a variety of materials may be selected for use as material 90. According to an exemplary embodiment, material 90 is a humectant having a predetermined water activity level (aW %). Material 90 will absorb or release water until an equilibrium point is reached in the collection device and in the cap or member 60. The humectant may be chosen so that a water activity level that is optimum for biological materials is maintained. According to an exemplary embodiment, the humectant 90 is chosen to maintain a water activity level between approximately 30-75%. According to a particular exemplary embodiment, a water activity level of approximately 65% is used. According to other exemplary embodiments, the water activity level may be between approximately 23% and 81%. The use of humectant materials has the advantageous result of maintaining living material within collection device 10 while preventing or limiting growth of the material.

According to an exemplary embodiment, the material 90 is a humectant formed from a mixture of a salt that is hydrated with a liquid (e.g., water) to provide the desired water activity level. According to an exemplary embodiment, the humectant comprises a mixture of water and a salt selected from the following: Calcium Bromide, Lithium Iodide, Potassium Acetate, Potassium Fluoride, Sodium Iodide, Potassium Carbonate, Magnesium Nitrate, Sodium Bromide, Cobalt Chloride, Potassium Iodide, Strontium Chloride, Sodium Nitrate, Ammonium Chloride, Ammonium Sulfate.

According to the embodiment of FIGS. 5-8, the first membrane 92 allows vapor to pass between the material 90 and the collection device 10. The first membrane 92 contains and separates the material 90 from collection device 10, and may be formed of any material that allows for two-way vapor transmission. According to an exemplary embodiment, the membrane is made from a porous plastic material (e.g., polypropylene, polyethylene, nylon, polycarbonate, polyvinylchloride, etc.). According to other exemplary embodiments, the membrane may be made of a metal (e.g., an aluminum member with apertures or holes provided therein), a porous paper material, or any other suitable material. The thickness, shape, size, porosity and other characteristics of the first membrane 92 may vary according to various exemplary embodiments.

A second membrane 91 may also be provided that provides further containment and separation of material 90 from collection device 10. The second membrane 91 may be comprised of a spunbonded olefin such as Tyvek® or another appropriate material such as those described with respect to membrane 92. The thickness, shape, size, porosity and other characteristics of the second membrane 91 may vary according to various exemplary embodiments.

Figures 9, 10:
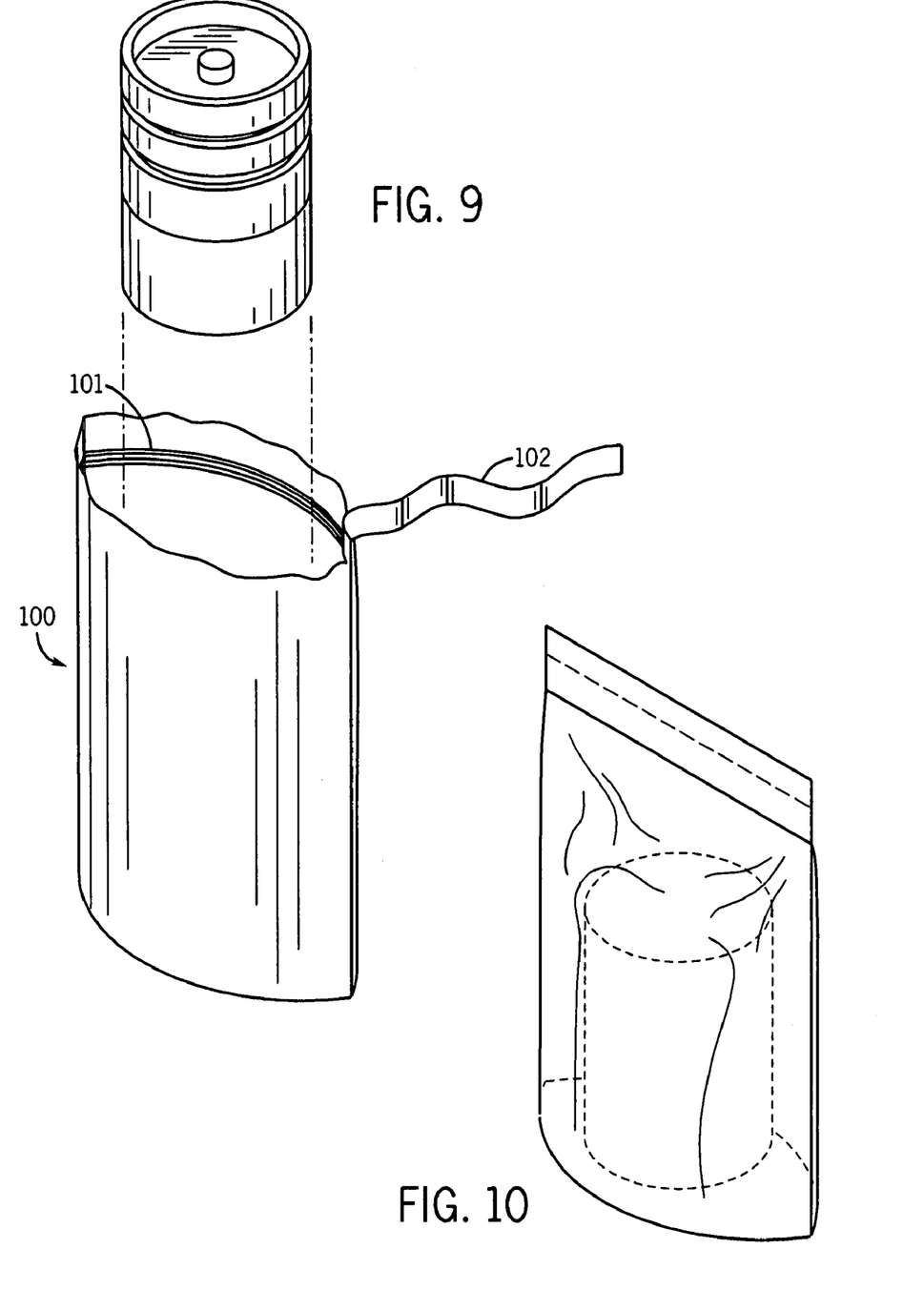
FIG. 9 is a perspective view of a pouch for holding the collection device according to an exemplary embodiment.
FIG. 10 is another perspective view of the pouch shown in FIG. 9.
Figure 11:
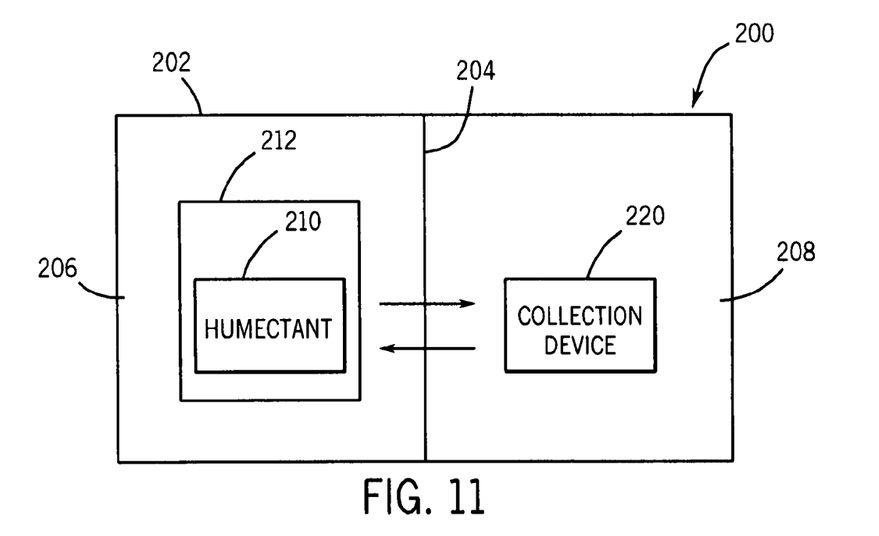
FIG. 11 is a schematic diagram illustrating a system for maintaining humidity in a collection device according to an exemplary embodiment.
Figure 12:
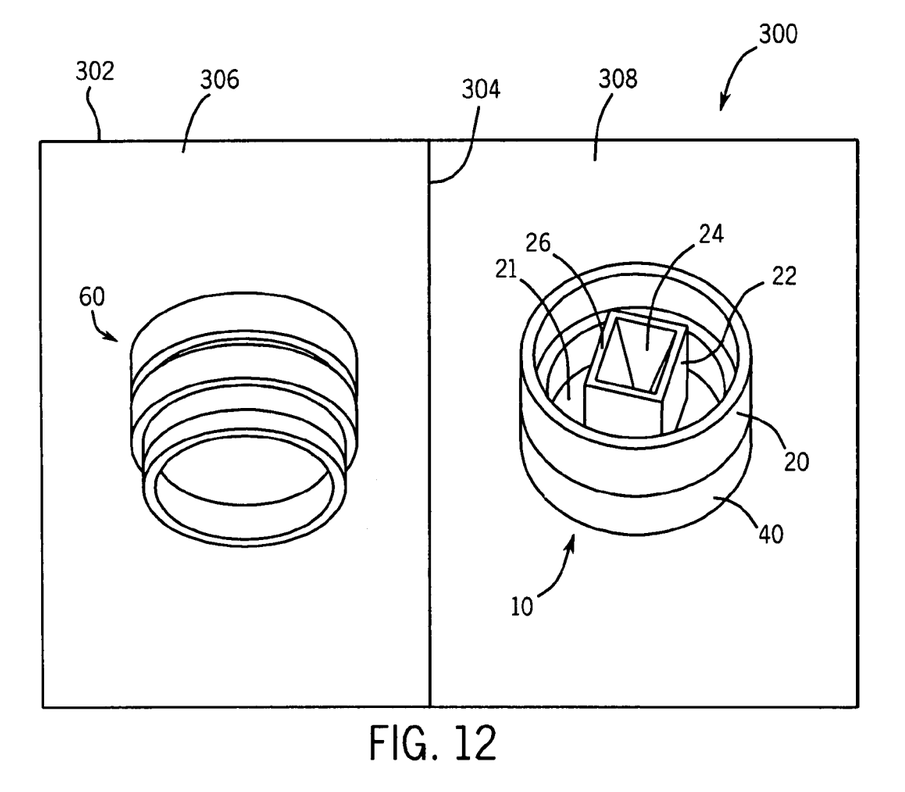
FIG. 12 illustrates a system for maintaining humidity in a collection device according to another exemplary embodiment.
Figure 13:
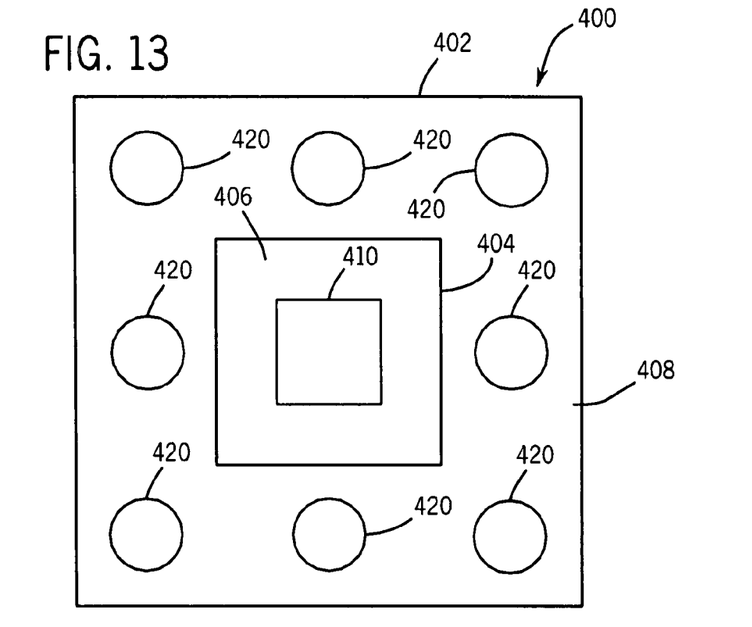
FIG. 13 illustrates a system for maintaining humidity in a collection device according to another exemplary embodiment.

According to an exemplary embodiment as shown in FIGS. 9-10, member 60 may be packaged in a pouch 100 that serves as a vapor barrier so the exposure to moisture during shipment and storage may be limited. The pouch 100 may be manufactured of a foil material or other suitable material. According to an exemplary embodiment, the pouch is formed of foil (e.g., aluminum foil) that is coated with another material (e.g., mylar, polyester, polypropylene, etc.). According to another exemplary embodiment, the pouch is formed of a metal-impregnated polymer (e.g., aluminum-dusted polypropylene).

The member 60 may be placed in the pouch 100 and the open end 102 closed or sealed by any standard method including but not limited to being heat sealed. The pouch 100 may also comprise a closing element 101 that may be resealed such as two plastic strips that fit into each other on the inner surface of the pouch 100. After the heat seal is broken, the closing element 101 may be used to reseal the pouch 100.

Collection device 10 may be utilized in a variety of different manners according to various exemplary embodiments. For example, in a first exemplary embodiment, collection device 10 may include a plate similar to plate 50 described above. The plate may be a clean substrate made of glass or another suitable material. Air sampling may be performed in such a manner that particles or other matter carried in the air are impacted directly onto the clean plate (i.e., the plate has no suspension material or other substance provided thereon). After sampling is completed, the plate may be directly sampled to an agar or other growth medium for culturing.

According to another exemplary embodiment, collection device 10 may include a plate similar to plate 50 described above, which may either be clean or may have a substance such as substance 54 or another substance provided thereon for capturing airborne matter. Airborne matter sampled onto the plate may then be suspended by adding a liquid such as water or peptone water to the collection device and retaining it therein (e.g., by plugging the inlet and outlet, etc.). Subsequent to sampling and suspension, the collection device may be drained and the liquid may be utilized with any of a variety of growth mediums for a variety of different tests (e.g., agar culturing, ELISA testing, PCR testing, etc.).

Various modifications may be made to collection device 10 that may allow for optimization for a particular use. For example, while the size of the opening at the bottom portion 28 of inlet 22 may be changed depending on the size and/or type of materials being sampled. In applications in which mold spores will be sampled, for example, the opening may have a length of approximately 0.6 inches and a width of approximately 0.030 inches. For a collection device that will be used in the collection of nanoparticles, the width of the bottom portion 28 of inlet 22 may be between approximately 0.001 and 0.005 inches. Virus sampling may utilize a width of the bottom portion 28 of inlet 22 may be between approximately 0.005 and 0.020 inches. Bacteria sampling may utilize a width of the bottom portion 28 of inlet 22 may be between approximately 0.015 and 0.025 inches. According to other exemplary embodiments, the size of the bottom portion of the opening may be optimized for the particular use and may have a different shape and/or size.

According to another exemplary embodiment, the material (e.g., humectant) for maintaining the humidity level of the sampled matter may be provided such that the material is not provided in a cap coupled to a collection device. In this manner, the humidity level of the sampled matter can be maintained at a desired level without the use of a cap such as that shown in FIG. 6.

FIG. 11 is a schematic diagram of a system 200 that includes a container or housing 202 that includes a first compartment or portion 206 and a second compartment or portion 208. The container 202 (and other such containers as will be described below according to other exemplary embodiments) may be used for storage and/or shipping of the collection devices, and according to an exemplary embodiment are configured so that they may be sealed in vapor-tight fashion (e.g., the interior of the container will have an environment substantially unaffected by the humidity level external to the container when the container is sealed). Alternatively, the entire container may be sealed within a vaporproof pouch or container.

The first compartment 206 is separated from the second compartment 208 by a structure such as a wall or divider 204. All or a portion of the wall 204 may be configured to allow two-way transmission of vapor between the first compartment 206 and the second compartment 208 (as illustrated by arrows in FIG. 11). For example, all or a portion of the wall 204 may be formed of a membrane material similar to those described above with respect to membranes 91 and 92. According to other exemplary embodiments, all or a portion of the wall may include apertures or holes formed therein to allow two-way transmission of vapor.

According to an exemplary embodiment, a material 210 (e.g., a humectant) is provided within the first compartment 206. A container 212 may optionally be provided for containing or storing the material 210. For example, FIG. 13 illustrates a system 300 in which the cap 60 illustrated in FIG. 6 is provided in a first compartment 306 of a container 302 and is separated from a second compartment 308 by a wall 304. Of course, those reviewing this disclosure will appreciate that the particular configuration of the container 212 may vary according to other exemplary embodiments.

A collection device 220 is provided in the second compartment 208. According to one embodiment as shown in FIG. 12, the collection device is similar to that shown in FIG. 1. According to other exemplary embodiments, the form of the collection device may differ.

One advantageous feature of the embodiment shown in FIGS. 11-12 is that the containers 202, 302 provide a humidity-controlled environment in which the collection devices may be stored and/or shipped (before and/or after sampling has been completed). That is, because the wall dividing the compartments allows for two-way transmission of vapor, an equilibrium point may be reached within the containers 202, 302 that is suitable to maintain the collected matter at a desired humidity level (or, where the collection devices have not yet been used for sampling, the collection devices may be maintained at a desired humidity level).

It should be understood that various modifications may be made to the embodiments shown in FIGS. 11-12. For example, according to an exemplary embodiment, a single humectant material may be provided to control the humidity for a plurality of collection devices. There are a number of ways that such an embodiment may be accomplished. In one system 400 shown in FIG. 13, a humectant 410 may be provided in a compartment 406 of a container 402. The compartment 406 is defined by walls 404 (all or a portion of which may be configured to allow for two-way transmission of vapor) with a plurality of collection devices 420 provided in an adjacent compartment 408.

Figure 14:
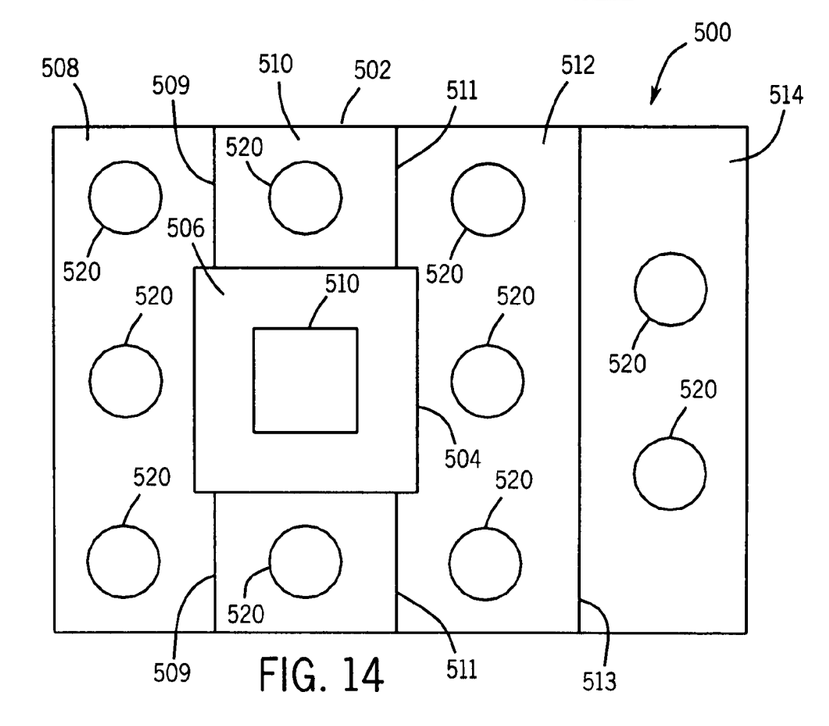
FIG. 14 illustrates a system for maintaining humidity in a collection device according to another exemplary embodiment.

In another system 500 shown in FIG. 14, a humectant 510 may be provided in one compartment 506 defined by walls 504 (all or a portion of which may be configured to allow for two-way transmission of vapor). The remainder of the container 502 may be subdivided into additional compartments (e.g., compartments 508, 510, 512, and 514 shown in FIG. 14). Such compartments may be adjacent the compartment 506 in which the humectant is provided and/or adjacent to other compartments. Walls 509, 511, and 513 separating adjacent compartments may be configured to allow for two-way transmission of vapor according to an exemplary embodiment. In this manner, humectant material may be contained in one area while providing humidity-controlling functionality for various separate compartments within the container. As shown in FIG. 14, compartments may include one or more collection devices.

Figure 15:
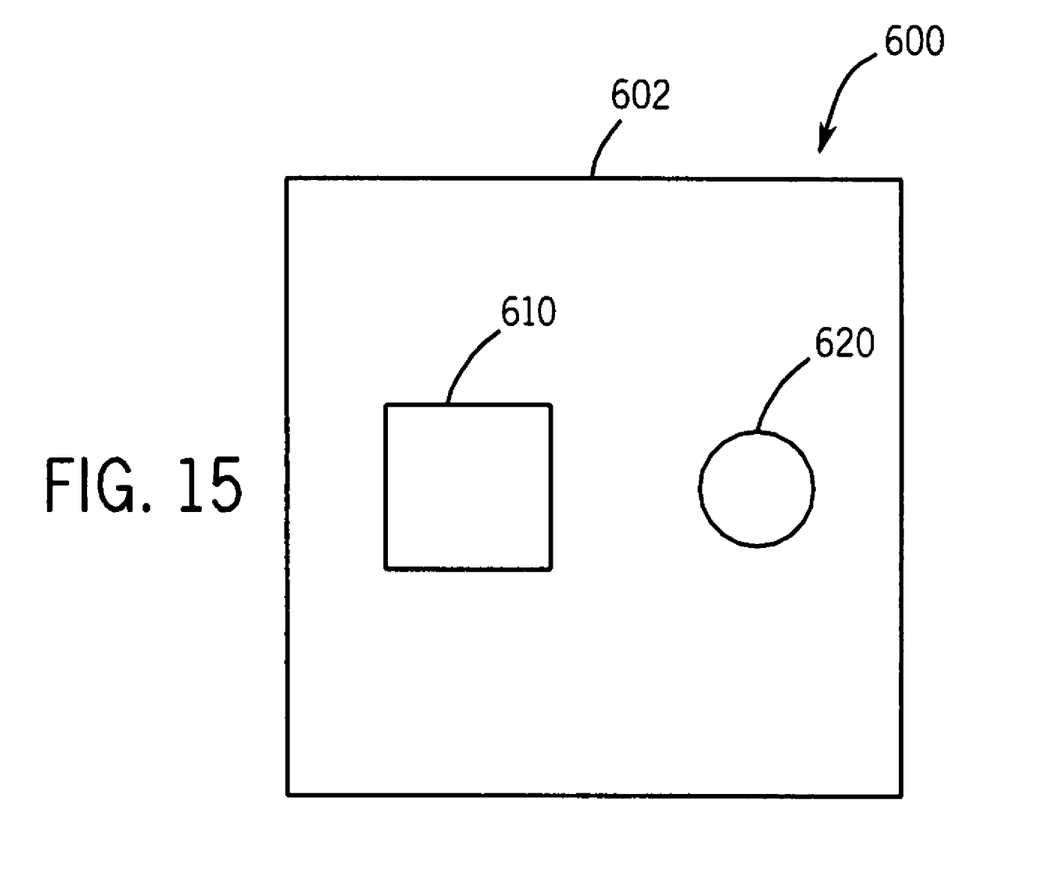
FIG. 15 illustrates a system for maintaining humidity in a collection device according to another exemplary embodiment.

According to other exemplary embodiments, humectants and collection devices may be provided in a single compartment, as shown in FIG. 15, in which a system 600 includes a container 602 in which a humectant 610 and a collection device 620 are provided in a single area. In the embodiment shown in FIG. 15, there are no internal subdivisions of the container 602 into separate compartments, although it should be understood that in a container having multiple compartments, one or more of such compartments may include both collection devices and humectant (and the humectant may or may not be stored in a container of its own).

The size, shape, location, and configuration of the various containers and compartments in such containers may also vary according to numerous other exemplary embodiments, and such alternative configurations are intended to fall within the scope of the present disclosure.

As those of skill in the art will appreciate, various advantages may be obtained using a collection device and/or suspension medium as described herein. For example, it is intended that because the collection device may be provided in a single-use form, there is no need to reload the collection device with a slide having new media provided thereon. It is also intended that the need to clean the slide or plate between uses is also eliminated. Further, it is intended that the risk of cross-contamination is reduced since the collection device is packaged in a relatively sterile environment and the slides or plates are not re-used. Contamination from the open environment may also be reduced, since the collection device may be sealed prior to shipping to the end user.

Other advantages may also be obtained. The collection device may be provided such that it is relatively compact and lightweight, which may allow it to be used in relatively tight or confined spaces. The configuration of the collection device may allow the device to be used with relatively low backpressure as compared to other devices which may require relatively large vacuum pumps to pull air through them.

The sampling medium (e.g., suspension medium) may be provided such that it need not be refrigerated, which may allow for simpler transport and storage. It is also intended that the sampling medium will have a relatively long shelf life as compared to other sampling media, and that it may be utilized to suspend the sample in a liquid or to archive the suspended solution. Further, it is intended that the sampling medium may act to eliminate or reduce the occurrence of dessication and destruction of organisms or other viable matter.

The construction and arrangement of the elements of the collection device as shown in the preferred and other exemplary embodiments is illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, orientations, etc.) without materially departing from the novel teachings and advantages of the subject matter recited herein. For example, elements shown as integrally formed may be constructed of multiple parts or elements, the position of elements may be reversed or otherwise varied, and the nature or number of discrete elements or positions may be altered or varied. It should be noted that the elements and/or assemblies of the system may be constructed from any of a wide variety of materials that provide sufficient strength or durability, including any of a wide variety of moldable plastic materials in any of a wide variety of colors, textures and combinations. The order or sequence of any process or method steps may be varied or re-sequenced according to alternative embodiments. Other substitutions, modifications, changes and omissions may be made in the design, operating conditions and arrangement of the preferred and other exemplary embodiments without departing from the scope of the present invention.

What is claimed is:

1. A system comprising:
   a sampling cassette having a plate provided therein for collecting gas-borne matter; and
   a humectant provided external to the sampling cassette for maintaining a desired humidity level for collected matter in the sampling cassette.

2. The system of claim 1, wherein the humectant has a water activity level of between approximately 23% and 81% and comprises water and a salt selected from the group consisting of Calcium Bromide, Lithium Iodide, Potassium Acetate, Potassium Fluoride, Sodium Iodide, Potassium Carbonate, Magnesium Nitrate, Sodium Bromide, Cobalt Chloride, Potassium Iodide, Strontium Chloride, Sodium Nitrate, Ammonium Chloride, and Ammonium Sulfate.

3. The system of claim 1, further comprising a member coupled to the ice sampling cassette, the member containing the humectant.

4. The system of claim 3, wherein the member comprises at least one porous membrane for physically separating the humectant from the sampling cassette and configured to allow water vapor to flow between the sampling cassette and the humectant.

5. The system of claim 3, wherein the member is a container comprising an upper portion and a lower portion that are removably coupled together.

6. The system of claim 1, further comprising a container, wherein the device sampling cassette and the humectant are provided within the container.

7. The system of claim 6, wherein the container comprises a first compartment and a second compartment, the device sampling cassette provided in the first compartment and the humectant provided in the second compartment, wherein the first compartment is separated from the second compartment by a membrane that is configured to allow water vapor to travel between the first compartment and the second compartment.

8. A system for controlling the humidity in a gas-borne matter collection sampling cassette, comprising:
   a member configured for coupling to a gas-borne matter collection sampling cassette; and a material provided within the member for maintaining a predetermined level of humidity within the collection sampling cassette.

9. The system of claim 8, wherein the material is a humectant having a water activity level of between approximately 23% and 81% and comprising water and a salt selected from the group consisting of Calcium Bromide, Lithium Iodide, Potassium Acetate, Potassium Fluoride, Sodium Iodide, Potassium Carbonate, Magnesium Nitrate, Sodium Bromide, Cobalt Chloride, Potassium Iodide, Strontium Chloride, Sodium Nitrate, Ammonium Chloride, and Ammonium Sulfate.

10. The system of claim 8, wherein the member comprises an upper part and a lower part that are removably coupled to each other.

11. The system of claim 8, wherein the material is physically separated from the collection sampling cassette by a porous membrane.

12. A system comprising:
a housing configured for selective coupling to a gas-borne matter collection sampling cassette; and
a humectant material provided within the housing for maintaining a predetermined level of humidity within the collection sampling cassette;
wherein the housing comprises a structure for physically containing the humectant material while allowing two-way vapor transmission between the humectant material and the collection sampling cassette.

13. The system of claim 12, wherein the humectant material has a water activity level of between approximately 30% and 75%.

14. The system of claim 12, wherein the structure comprises a membrane.

15. The system of claim 12, further comprising a collection sampling cassette, wherein the housing and the collection sampling cassette are provided in a container.

16. The system of claim 12, further comprising a collection sampling cassette, wherein the housing and the collection sampling cassette are provided in a vapor impermeable pouch.

17. A system for collecting viable gas-borne matter, the system comprising:
a sampling cassette comprising at least one inlet, at least one outlet, and a plate provided intermediate the inlet and outlet;
a substance provided on the plate for capturing viable matter carried in a gas drawn through the at least one inlet;
a cap configured for coupling to the cassette;
a humectant provided in the cap for maintaining a predetermined level of humidity within the cassette; and a membrane provided between the humectant and the cassette that allows gas and vapor to move between the substance and the humectant;

wherein the humectant is configured to regulate the water activity level such that viable matter is maintained in a living state without promoting growth of such viable matter.

18. The system of claim 17, wherein the humectant has a water activity level of between approximately 23% and 81% and comprises water and a salt selected from the group consisting of Calcium Bromide, Lithium Iodide, Potassium Acetate, Potassium Fluoride, Sodium Iodide, Potassium Carbonate, Magnesium Nitrate, Sodium Bromide, Cobalt Chloride, Potassium Iodide, Strontium Chloride, Sodium Nitrate, Ammonium Chloride, and Ammonium Sulfate.

19. The system of claim 17, wherein the sampling cassette comprises a top portion connected to a bottom portion.

20. A system comprising:

a container;

a gas-borne matter collection device in the form of a sampling cassette provided within the container; and a humectant material provided within the container, the humectant material configured to maintain a humidity level within the container and within the gas-borne matter collection device.

21. The system of claim 20, wherein the humectant material is provided within a housing configured for coupling to the gas-borne matter collection device.

22. The system of claim 20, wherein the container includes a first portion and a second portion, and wherein the gas-borne matter collection device is provided in the first portion and the humectant material is provided in the second portion.

23. The system of claim 22, wherein the first portion is separated from the second portion by a structure configured to allow two-way water vapor transmission.

24. The system of claim 22, wherein the container further comprises a third portion, the third portion including at least one of a humectant and a collection device.

* * * * *